United States Patent [19]
Schilling et al.

[11] Patent Number: 6,015,920
[45] Date of Patent: Jan. 18, 2000

[54] HYDROSILATION REACTION PROCESS WITH RECYCLE

[75] Inventors: Curtis L. Schilling, Marietta, Ohio; Patrick James Burns, Parkersburg, W. Va.; James Stephen Ritscher; Mark Paul Bowman, both of Marietta, Ohio; Thomas Edgeworth Childress, Newport, Ohio; Michael Ray Powell, New Martinsville, W. Va.; Eric Michael Graban, Marietta, Ohio

[73] Assignee: CK Witco Corporation

[21] Appl. No.: 09/151,642

[22] Filed: Sep. 11, 1998

[51] Int. Cl.[7] ....................................................... C07F 7/08
[52] U.S. Cl. ............................................................ 556/479
[58] Field of Search ................................................ 556/479

[56] References Cited

U.S. PATENT DOCUMENTS

| | | | |
|---|---|---|---|
| 5,041,595 | 8/1991 | Yang et al. | 556/479 |
| 5,616,762 | 4/1997 | Kropfgans et al. | 556/479 |
| 5,756,795 | 5/1998 | Bank et al. | 556/479 |

*Primary Examiner*—Paul F. Shaver
*Attorney, Agent, or Firm*—Edward K. Welch, II; Andrew S. Reiskind

[57] ABSTRACT

A process for hydrosilation reactions between olefins and hydrosilanes or hydrosiloxanes wherein a portion of the reactor output is recycled continuously to the reactor.

13 Claims, No Drawings

HYDROSILATION REACTION PROCESS WITH RECYCLE

BACKGROUND OF THE INVENTION

The present invention relates to the reaction, known as hydrosilation, in which a silane or polysiloxane which is substituted with hydrogen and with halogen, alkyl and/or alkoxy groups is reacted with an olefin. This invention is directed in particular to hydrosilation of silanes, but can include also other species as discussed below.

The reaction of hydrosilatable olefins, such as allyl chloride or 1-octene, with hydrosilanes such as trimethoxysilane, in the presence of an appropriate catalyst, is known. An example is disclosed in U.S. Pat. No. 5,559,264, which is directed to the reaction of allylic chloride with hydromethoxysilane in the presence of ruthenium catalyst. A continuous hydrosilation process with recycle is disclosed in German Offen. 196-32157 Al, wherein conversion of the limiting reactant is limited to less than 80% to minimize a side reaction inherent to hydrosilation reactions between chlorosilanes and allyl chloride. Limiting conversion to less than 80% is a disadvantage for hydrosilation reactions not afflicted with significant side reactions.

There is interest in finding improved modes of carrying out the hydrosilation reaction. Improvements are elusive because of the variety of byproducts that typically are formed, their properties, and the need to control their formation and to remove those that do form from the desired silane product. In addition, the hydrosilation reaction itself is sensitive to a number of conditions such that it can become necessary to balance competing effects and to accept non-optimum results.

Certain process schemes for carrying out the hydrosilation reaction, while effective, pose drawbacks. For instance, typical batchwise operation produces a crude product containing the desired hydrosilated silane product in mixture with byproducts and one or more unreacted reactants. This crude product needs to be treated to recover the desired product in a subsequent stage, and it needs to be stored until it is passed to that stage. This storage, even temporary, poses a risk of degrading of the product, as well as a risk of the crude product undergoing cross-reaction with potentially hazardous and even explosive effect. Also, storing crude product within the reaction scheme represents an accumulated inventory of material which raises the overall cost of the process. If the crude product contains substantial amounts of unreacted silane, safety considerations may dictate more costly equipment for handling or storage.

SUMMARY OF THE INVENTION

The present invention is a continuous process for carrying out a hydrosilation reaction, which has the steps of:
  (a) feeding a hydrosilatable olefin and a hydrosilane or hydrosiloxane (or mixtures of the hydrosiloane and hydridosiloxane) capable of reacting with the olefin into a reactor containing a stoichiometric excess of one of the reactants in the presence of a catalytically effective amount of a hydrosilation catalyst;
  (b) reacting said olefin with said hydrosilane or hydrosiloxane in the reactor, whereby at steady state an unreacted excess of one of the reactants is maintained, to form a hydrosilated product;
  (c) withdrawing from said reactor a product stream;
  (d) purifying said product stream to produce a recycle stream including said unreacted reactants, and a product stream; and
  (e) recycling the recycle stream into the reactor; and wherein the conversion of the stoichiometrically limiting reactant in the reactor is greater than 80%.

DETAILED DESCRIPTION OF THE INVENTION

The olefin reactant with which the process of this invention is carried out can be any that reacts with a hydrosilane or hydrosiloxane in the desired reaction. By olefin, not only are unsaturated hydrocarbons meant, but any compound which has an ethylenic or acetylinic unsaturatations which may be hydrosilized, including, but not limited to acetylene, $\alpha$, $\omega$-diolefins, and allyl started materials. Preferred examples of the olefin are allyl chloride and methallyl chloride. Other olefin reactants useful in this reaction include: 1-octene, 1-hexene, amylene, 1-octadecene, allyl glycidyl ether, vinylcyclohexene monoxide, allyl (meth) acrylate, perfluorooctylethylene, acrylonitrile, and unsaturated silanes such as vinyltrimethoxysilane and allyltriethoxysilane. Other examples are low molecular weight terminally unsaturated poly(alkylene oxides) with a terminal group such as allyl and a chain of repeating ethylene oxide and/or propylene oxide units.

The hydrosilane reactant useful in this reaction can be any that reacts with the olefin. The hydrosilane may be characterized by the formula HSiXYZ wherein X, Y and Z are independently of one another a hydrocarbon or alkoxy group, typically containing up to eight (8) carbon atoms, hydrogen or halogen. The hydrocarbon may be branched, linear, cyclic or aromatic. Preferably the hydrocarbon is a linear or branched alkyl e.g., methyl and ethyl. Preferred alkoxy groups are methoxy and ethoxy, though branched structures may be used. X, Y and Z can be halogen (especially chloride), and one of X, Y or Z can be a second hydrogen atom. Particularly preferred hydrosilanes are trimethoxysilane and trichlorosilane. Other preferred hydrosilanes include trimethylsilane, methyldimethoxysilane, dichlorosilane, triethoxysilane, methyldiethoxysilane, methyldichlorosilane, dimethylchlorosilane, and di-methylmethoxysilane.

The hydrosiloxane reactants useful in the above process can be described by the general formula, HSiABC, where at least one of A, B, and C are a siloxy group, —OSiXYZ where X, Y, and Z are as above or a further siloxy group (to form a siloxane chain) and the others of A, B and C are selected from X, Y and Z above or two of A, B and C taken together may be a divalent siloxy group —O(SiXYO)$_n$- where X and Y are lower alkyl groups, preferably methyl, and n is 3, 4, or 5.

The olefin and hydrosilane or hydrosiloxane reactants are fed continuously, i.e., as a continuous stream or a pulsed, intermittent stream, to a reactor for hydrosilation reactions. A catalyst for the hydrosilation reaction should be present in an amount effective to catalyze the reaction of the olefin with the hydrosilane or hydrosiloxane. Examples of suitable catalysts are known in the literature and are typically compounds of metals such as palladium, platinum, ruthenium, osmium, rhodium, or iridium. A preferred catalyst is any of the ruthenium compounds disclosed in the aforementioned U.S. Pat. No. 5,559,264. Effective amounts of the catalyst can be determined readily and are on the order of 5 to 50 ppm based on the total amount of reactants present.

The molar amounts of olefin and hydrosilane or hydrosiloxane relative to each other in the reactor feeds can vary somewhat depending on the degree of side reactions which may consume one or the other reactant, and will also need to be determined with reference to the amounts of each reactant present in the recycle stream described hereinbelow. Conveniently the olefin and hydrosilane or hydrosiloxane can be fed in stoichiometrically equivalent amounts, but an excess of one reagent may be required to maintain the conditions outlined below. The amount of excess required may be determined by one of ordinary skill in the art, based on mass balance of the end product.

Within the reactor, operating at steady state, one or the other reactant is in molar excess, preferably, at least 3:1 molar ratio. By virtue of the immediate recycle of excess reagent removed from the reactor, the steady state excess of said reagent is maintained. The relative amounts of the hydrosilane or hydrosiloxane and olefin reactants within the reactor during steady state operation are such that an excess of either the hydrosilane or hydrosiloxane reactant or the olefin is maintained. The choice of which reactant to maintain in excess will depend upon factors such as cost, efficiency of the hydrosilation reaction at various stoichiometries, and formation of byproducts in the presence or absence of the excess reagent. When the hydrosilane or hydrosiloxane is in excess, the molar ratio of it to olefin in the reactor preferably should be in the range of about 10:1 to about 1000:1 or more, with a preferred more narrow range being about 20:1 to about 500:1. Likewise, when the olefin is maintained in excess in the reactor, it should be in the molar ratio range of about 5:1 to about 10:1, with a preferred more narrow range being about 5:1 to about 100:1. When the hydrosilane or hydrosiloxane is in excess, the steady state molar ratio of it to product will be in the range of about 0.1:1 to about 3:1; when the olefin is in excess, the ratio of it to product will be in the range of about 0.01 to about 0.5:1.

It has been found in some cases that it is preferable to combine the catalyst with the hydrosilane or hydrosiloxane, prior to introduction of the hydrosilane or hydrosiloxane into the reactor. This can be accomplished by adding a solution of the preferred catalyst to the hydrosilane or hydrosiloxane via a mix-tee upstream to the latter's entry to the reactor. The length of pipe after mixing will determine contact time, and insulation and/or heating of the pipe will determine the temperature, and are easily varied. Optimum conditions for addition of the catalyst in this fashion may vary with different hydrosilations. In other cases, the catalyst solution may be fed directly to the reactor to maintain the desired steady state concentration of catalyst within the reactor.

The reactor contents are preferably free of solvent. If desired, one may add a solvent for the reactants and/or reaction product; but in this case, the solvent should preferably be one which will be recycled to the reactor along with the excess reactant. Otherwise, the solvent will exit the purifier with the product stream, and would need to be replenished to the reactor by feeding a separate solvent stream, recycling a solvent stream separated from the product stream, or cofeeding the solvent along with the olefin or hydrosilane or hydrosiloxane reactant. Suitable solvents include toluene, dichloromethane, hexane, and tetramethoxysilane. However, if the solvent interferes with catalytic activity, then use of a solvent is contraindicated.

The reaction of the olefin with the hydrosilane or hydrosiloxane is carried out under effective conditions of temperature and pressure with agitation, preferably by stirring. Preferred reaction conditions include a temperature from about ambient temperature up to about 150° C., with 60 to 120° C. being most preferred. Generally, the process is carried out at a pressure of about 0.2 to 2.0 atmospheres (0.02–0.2 MPa), with ambient pressure being preferred, but operation at higher or lower pressures may be performed to maintain higher or lower reaction temperatures dependent on the volatilities of the respective reactants.

The residence time within the reactor is not critical but should be sufficient to achieve a satisfactory degree of conversion to the hydrosilated product, i.e., >80%, within acceptable limits given the volume of the equipment and the desired rate of production. Typical acceptable residence times are on the order of 0.5 to 4 hours.

The hydrosilation reaction product is formed by attachment of the hydrogen atom of the hydrosilane or hydrosiloxane and the silicon atom of the silane across the unsaturated site of the olefin, as is well known. For example, hydrosilation of allyl chloride with trimethoxysilane forms 3-chloropropyl-trimethoxysilane. Examples of other preferred hydrosilation reaction products that can be formed in this process from appropriately selected reactants include n-octyltrichlorosilane; glycidoxypropylmethyldimethoxysilane; [epoxycyclohexyl]ethyltriethoxysilane; cyanoethyltrichlorosilane; dihexyldichlorosilane; amyltrimethoxysilane; triethoxysilylethyltriethoxysilane and [perfluorooctyl]ethylmethyldiethoxysilane.

A crude product stream is established which exits the reactor, typically through a pipe or tube terminating at or near the bottom of the reactor. This product stream contains hydrosilated olefin reaction product and either unreacted olefin, unreacted hydrosilane or hydrosiloxane, or both, catalyst, reaction byproducts and a solvent, if used. The flow rate should be such that the amount of liquid volume, and consequently hydrosilated reaction product, within the reactor remains approximately constant, as does the acceptable residence time for the hydrosilated reaction product.

The crude product stream is fed to a purifier, wherein the product and reactants are separated. The purifier produces two streams: a recycle stream which contains essentially all the unreacted olefin or essentially all the unreacted hydrosilane or hydrosiloxane, or both, that are fed to the purifier (and the solvent, if used), and a purified product stream which contains the hydrosilated reaction product. The purifier operates at an effective combination of temperature and pressure to achieve the desired separation between the unreacted reactants and the reaction product. The purifier may be a distillation column or stripping column with or without packing, trays, or plates, a decanter, a wiped film evaporator, or other unit known in the separation art.

This process provides several advantages. The prompt separation of the unreacted materials from the crude product stream reduces the risk of continued side reactions and the resultant risks of product degradation and runaway reactions. The recycle of the unreacted reactants also increases the efficiency with which the materials are used, and lowers the overall amount of devices tied up in carrying out the production of the desired hydrosilation reaction product. Also, this process avoids the general need for any solvent, although such solvent may be deemed beneficial in selected cases.

Typical efficiencies in the overall process range from 85–98%. That is, the purity of the product stream exiting from the purifier is between 85% and 98% by weight of reaction product. This stream includes product, any heavy by-products, traces of unreacted olefin and hydrosilane or hydrosiloxane, and catalyst residues. The product stream subsequently may be distilled, thus recovering an even more pure product stream, generally from 95–99.9% by weight of product; a lights stream containg lower boiliing impurities, by-products, and olefin and hydrosilane or hydrosiloxane starting materials; and a heavies stream containing higher boiling by-products, and the residues of the catalyst. The lights and heavies streams may be discarded, although the noble metal catalyst may be recovered by chemical treatment.

In the recycle stream that returns to the reactor, there will be excess hydrosilane or hydrosiloxane (if used in excess) and varying amounts of olefin (the amount depending on residence time in the reactor, or olefin (if used in excess) and varying amounts of hydrosilane or hydrosiloxane (the amount depending on the residence time in the reactor). The advantage of this invention is that the amount of olefin or hydrosilane or hydrosiloxane may vary, without being detrimental to the performance of the reactor. In fact, the reactor system is designed to allow for variation, and thus provide much greater flexibility in the operation of the unit.

This same recycle stream preferably should not contain any of the product. Although the presence of product, per se, is not detrimental to the functioning of the process, such presence would tend to indicate that the purifier is being operated under non-optimal conditions. The ratio of the amount of material in the recycling stream of the purifier to the amount of material in the product stream being drawn off will vary according to the particular hydrosilation being conducted, as well as the throughput. Practically, this ratio will not exceed one part of recycle stream to one part of product stream, i.e., 1.0:1.0 by weight, and preferably will be no greater than 0.5:1.0.

The operating conditions of the purifier, such as temperature, pressure, residence time, and pressure drop, will depend on the physical and chemical nature of the reactants and products, and on its design. The purifier can be any device of appropriate material of construction which is known in the art. Thus, a purifier which is a distillation column with a reboiler may contain structured packing, ceramic saddles, or trays, all of which will work equally well as long as no reaction between them, the product, or the starting materials occurs, and no product degradation is caused. Such factors must be determined for each individual case, and may even require experimentation to draw the proper conclusion as to material of construction. The reactor and ancillary parts may also be of any material of construction which will maintain its integrity against corrosion, thermal exposure, and pressure. The requirements of the present invention are no more stringent than for other standard silanes processing units known in the art.

Typical reactor/purifier designs, each of which may incorporate ancillary equipment for heating, cooling, maintaining pressure, agitation, metering of reactant feeds, maintenance of inert atmospheres, feed systems, and product receiving systems, include continuous stirred tank/distillation column combinations, static mixer reactor/wiped film evaporator combinations, plugged flow reactor/decanter combinations, and other combinations of the parts thereof. One preferred reactor/purifier design includes a continuous stirred tank reactor (CSTR) with feed tanks for the reactants, a column with a recycle line to the reactor and a reboiler, and product receivers.

As noted above, the process of the present invention can provide hydrosilation products at varying levels of efficiency. Preferably, one of the reagents is converted in the reactor to hydrosilation product at a high degree of conversion, for example greater than 90% by weight. The conversion is dependent on residence time in the reactor, and thus may be inversely porportional to feed rate. A high degree of conversion, i.e., not less than 80% of the limiting reactant, maximizes the yield of hydrosilation product and minimizes the volume of the recycle stream. However, as discussed above, the system may operate flexibly with lower conversion. Thus, increasing feed rate may not cause the reaction to stop, or lead to a dangerous buildup of unreacted starting materials in a product storage tank or a batch reactor, such as might occur with process technologies known in the art. Rather, the excess reagents, by virtue of being removed and then recycled immediately, cannot build up downstream of the purifier, even if process upsets occur, such as pressure fluctuation, or a stoichiometric imbalance in the reactant feeds.

It will be recognized by those skilled in the art that separation into recycle and product streams will not be absolute and that each stream may contain small amounts of the other. It is also recognized that each stream may require further separation to maximize utility, e.g., the product stream may be separated from the catalyst, as by distillation, to provide product of high purity and to provide the catalyst in a form which may also be recycled to the reactor. If the recycle stream contains an undesired by-product which increases in relative amount as the continuous reaction proceeds, it may be necessary to subject the recycle stream to a second separation, such as purging whereby said by-product is removed before the recycle stream re-enters the reactor.

The conditions of the various separations, including temperatures, pressures, times, equipment sizes such as columns, and separation efficiencies may vary substantially, depending on the physical properties of the various reactants and hydrosilation products.

The following are examples of operation of the process of the present invention. In the examples, the abbreviations g, ppm or ppmw, wt., and CSTR represent gram, parts per million by weight, weight, and continuous stirred tank reactor, respectively.

EXAMPLES

Example 1

Hydrosilation of Allyl chloride with Trimethoxysilane

Over the course of 32 hours, 3534.4 g of trimethoxysilane (TMS), 1786.2 g of allyl chloride and 11.5 g of catalyst solution (containing 2.94 wt. % ruthenium in the form of ruthenium chloride hydrate dissolved in methanol) were added to a 1-liter glass reactor. A constant level was maintained in the stirred reactor such that the residence time was about 2.8 hours. The reactor was maintained at about 75° C. The catalyst loading in the reactor was ~30 ppm of ruthenium, the ratio of TMS to 3-chloropropyltrimethoxysilane product, (CPTMS) in the reactor was 0.8:1. Water and dry ice condensers were used to keep low boiling materials from escaping from the reactor. On startup, the reactor contained CPTMS, TMS (in a ratio of about 1:0.8) and ruthenium chloride catalyst (30 ppm Ru).

The crude product in the reactor (at steady state) contained allyl chloride 0.08 wt. %, trimethoxysilane 20.8 wt. % and CPTMS 69.9 wt. % (GC). During continuous operation, the reactor effluent was continuously pumped to the $5^{th}$ tray from the bottom of a 15-tray Oldershaw column. The column reboiler was maintained at 175–180° C. The lights, consisting mainly of TMS with low levels of impurities, were recycled immediately back to the reactor. The crude product was pumped continuously from the reboiler to a separate flask.

After 32 hours of operation, 5254.8 g of crude product was collected. The crude product consisted of:

| | |
|---|---|
| TMS | 0.8 wt. % |
| ClSi(OMe)$_3$ | 0.5 wt. % |
| Si(OMe)$_4$ | 3.6 wt. % |
| Other low boiling materials | 2.0 wt. % |
| Propyltrimethoxysilane | 1.8 wt. % |
| Cl(MeO)$_2$SiCH$_2$CH$_2$CH$_2$Cl | 1.4 wt. % |
| (MeO)$_3$SiCH$_2$CH$_2$CH$_2$Cl | 87.3 wt. % |
| Higher boilers | 2.6 wt. % |

Example 2

Hydrosilation of Amylene with Trichlorosilane by Platinum Catalysis

Over the course of 6.5 hours, 1105 g (8.16 moles) of trichlorosilane and 525 g (7.49 moles) of amylene were fed into a flask (4.7 reactor volume turnovers) initially containing: 2 wt. % trichlorosilane, 7 wt. % amylene and 90% amyltrichlorosilane. A platinum catalyst continuously was added to the reactor to maintain a platinum concentration of 34 ppmw. The catalyst was a divinyltetramethyldisiloxane platinum complex dissolved in a dimethylsilicone fluid (2 wt. % Pt). The reactor temperature was held between 57–71° C.

At steady state, the reaction crude contained amylene isomers 15.9 wt. %, trichlorosilane 0.12 wt. % and amyltrichlorosilane 72.6 wt. % (82% conversion of amylene). The reaction crude was fed to the middle of a 12×0.5 inch (152.4 cm) column packed with 0.16×0.16 inch (0.80 cm) stainless steel saddles. The distillation lites were continuously recycled back to the reactor. The reboiler was kept at 160–164° C. A constant reboiler liquid level was maintained. The product exiting the reboiler contained 98.2% by weight amyltrichlorosilane (both isomers), unreacted amylene 0.3 wt. % and other low boiling materials 1.5 wt %.

Example 3

Hydrosilation of Allyl Chloride with Trimethoxysilane by Iridium Catalysis

Over the course of 4.5 hours, 680 g (5.57 moles) of trimethoxysilane and 459 g (5.93 moles) of allyl chloride were fed into a flask (3 reactor volume turnovers) initially containing: 8 wt. % allyl chloride, 3 wt. % trimethoxysilane, 5 wt. % chlorotrimethoxysilane, 12 wt. % tetramethoxysilane, 1.4 wt. % propyltrimethoxysilane, 3.7 wt. % chlorodimethoxypropylsilane and 61% chloropropyltrimethoxysilane. An iridium catalyst continuously was added to the reactor to maintain an iridium concentration of 23 ppmw. The catalyst was a methanol solution of dihydrogen hexachloroiridate(IV) hydrate (0.9 wt. % of the solid catalyst dissolved in methanol). The reactor temperature was held between 89–93° C. The reaction crude contained 64% by weight CPTMS, 0.08 wt. % allyl chloride and 20.5 wt. % TMS. The reaction crude was fed to the middle of a 12×0.5 inch (152.4 cm) column packed with 0.16×0.16 inch (0.80 cm) stainless steel saddles. The distillation lites were continuously recycled back to the reactor. The reboiler was kept at 179–180° C. A constant reboiler liquid level was maintained. The product exiting the reboiler contained 82.1 wt. % 3-chloropropyltrimethoxysilane, 5.7 wt. % Cl(MeO)$_2$CH$_2$CH$_2$CH$_2$Cl, 1.0 wt. % (MeO)$_3$SiCH$_2$CH$_2$CH$_3$, 6.4 wt. % tetramethoxysilane and 1.3 wt. % ClSi(OMe)$_3$ other high boiling materials 2.1 wt. % and other low boiling materials 1.4 wt. %.

Example 4

Hydrosilation of Octene with Triethoxysilane Catalyzed by a Platinum Catalyst

Over the course of 35 hours, 2429 g of triethoxysilane and 2111 g of 1-octene were fed into a flask (14 reactor volume turnovers) initially containing octyltriethoxysilane, 0.3 wt. % acetic acid and 5 ppmw of the below described platinum catalyst. A platinum catalyst continuously was added to the reactor to maintain an platinum concentration of 5 ppmw. The catalyst was a divinyltetramethyldisiloxane platinum complex dissolved in a dimethylsilicone fluid (2 wt. % Pt). Acetic acid also was fed continuously into the reactor to maintain 0.3 wt. % concentration in the CSTR. The reactor temperature was held at 100° C. The reaction crude contained triethoxysilane 0.26 wt. %, various octene isomers 18.3 wt. % total and octyltriethoxysilane 76.7 wt. %. The reaction crude was fed to the middle of a 20-tray Oldershaw column. The distillation lites were recycled continuously back to the reactor. The reboiler was kept at 230° C. A constant reboiler liquid level was maintained. The product exiting the reboiler contained triethoxysilane 0.008 wt. %, various octene isomers 5.0 wt. % total, tetraethoxysilane 2.8 wt. %, other low boiling materials 0.6 wt. %, octyltriethoxysilane 89.2 wt. % and other higher boiling materials 2.4 wt. %.

Example 5

Hydrosilation of Octene with Trichlorosilane Catalyzed by a Platinum Catalyst

In the apparatus of Example 4, over the course of 16 hours (8 reactor volume turnovers), trichlorosilane was reacted with 1-octene (90% molar excess) using 25 ppm platinum supplied as a platinum acetylacetonate solution. The product stream from the purifier had an average analysis of 93.6% purity as octyltrichlorosilane over the duration of the run.

Example 6

Hydrosilation of Styrene with Methyldichlorosilane Catalyzed by a Platinum Catalyst In the apparatus of Example 4, over the course of 10 hours (5 reactor volume turnovers, methyldichlorosilane (50 % molar excess) was reacted with styrene using 25 ppm platinum supplied as a chloroplatinic acid solution. The pot temperature was 75° C. and the reboiler temperature was 190° C. The product stream from the purifier contained 91.9% of a mixture of the nonterminal and terminal adducts of methyldichlorosilane to styrene.

Example 7

Hydrosilation of Octene with 1,1,1,3,5,5,5-Heptamethyltrisiloxane Catalyzed by a Platinum Catalyst In the apparatus of Example 4, over the course of 13.5 hours (9 reactor volume tunovers), heptamethyltrisiloxane was reacted with 1-octene (100% molar excess) using 5 ppm of platinum supplied as its complex with divinyltetramethyldisiloxane. The product stream from the purifier had an average analysis of 86.5% purity as octylheptamethyltrisiloxane over the duration of the run.

What is claimed is:

1. A process comprising:
   (a) feeding continuously a hydrosilatable olefin and a hydrosilane or hydrosiloxane capable of reacting with the olefin into a reactor;
   (b) reacting said olefin with said hydrosilane or hydrosiloxane in the reactor in the presence of a catalytically effective amount of catalyst to form a hydrosilated product;

(c) withdrawing continuously from said reactor a crude product stream, (d) separating said crude product stream in a purifier to produce
   (i) a recycle stream comprising unreacted olefin, or unreacted hydrosilane or hydrosiloxane, and
   (ii) a product stream comprising said hydrosilated product; and (e) recycling said recycle stream (d)(i) into said reactor; and wherein the conversion of the stoichimetrically limiting reactant in the reactor is greater than 80%.

2. The process of claim 1 wherein said olefin is allyl chloride and said hydrosilane is trimethoxysilane.

3. The process of claim 2 wherein said catalyst is a compound of ruthenium.

4. The process of claim 1 wherein said hydrosilane is selected from the group consisting of trichlorosilane, methyldichlorosilane, dimethylchlorosilane, trimethylsilane, dimethylmethoxysilane, methyldimethoxysilane, trimethoxysilane, triethoxysilane, methyldiethoxysilane, and dimethylethoxysilane.

5. The process of claim 1 wherein said hydrosiloxane is selected from the group of heptamethyltrisiloxane isomers, pentamethyldisiloxane, nonamethyltetrasiloxane isomers, heptamethylcyclotetrasiloxane, nonamethylcyclocyclopentasiloxane, tetramethyldisiloxane, octamethyltetrasiloxane isomers, undecamethylpentasiloxane isomers, and hexamethyltrisiloxane isomers.

6. The process of claim 1 wherein said hydrosilatable olefin is selected from the group consisting of allyl chloride, methallyl chloride, allyl and methallyl (meth)acrylates, allyl and methallyl polyethers, terminal alkenes, amylene, allyl glycidyl ether, vinylcyclohexene monoxide, perfluoroalkylethylenes, styrene, styrene derivatives, allyl amines, (meth)acrylonitrile, and (meth)acrolein derivatives vinyltrimethoxysilane, vinyltriethoxysilane, and allyltriethoxysilane, vinylmethyldimethosysilane and vinylmethyldiethoxysilane.

7. The process of claim 1 wherein said catalyst contains at least one metal selected from the group consisting of palladium, platinum, ruthenium, rhodium, osmium, and iridium.

8. The process of claim 7 wherein said catalyst is essentially insoluble and is present in the free metallic state or on an inorganic, organic, or metallic support.

9. The process of claim 1 further comprising the addition into the reactor of a carboxylic acid as a reaction promoter.

10. The process of claim 9 wherein said hydrosilane is triethoxysilane, said olefin is 1-octene, said catalyst is a divinyltetramethyldisiloxane platinum complex, and said carboxylic acid is acetic acid.

11. The process of claim 1 wherein said hydrosilane is trichlorosilane, said olefin is amylene, and said catalyst is a divinyltetramethyldisiloxane platinum complex.

12. The process in claim 1 wherein the catalyst is combined with the hydrosilane or hydrosiloxane prior to introduction of the catalyst into the reactor.

13. The process of claim 1 wherein one of the reactants is present in the reactor at a stoichiometric molar excess of at least 3:1.

* * * * *